(12) United States Patent
Puckette et al.

(10) Patent No.: US 6,906,225 B2
(45) Date of Patent: Jun. 14, 2005

(54) STABILIZATION OF FLUOROPHOSPHITE-CONTAINING CATALYSTS

(75) Inventors: Thomas Allen Puckette, Longview, TX (US); Ginette Struck Tolleson, Longview, TX (US)

(73) Assignee: Eastman Chemical Company, Kingsport, TN (US)

( * ) Notice: Subject to any disclaimer, the term of this patent is extended or adjusted under 35 U.S.C. 154(b) by 7 days.

(21) Appl. No.: 10/896,666

(22) Filed: Jul. 22, 2004

(65) Prior Publication Data

US 2004/0267036 A1 Dec. 30, 2004

Related U.S. Application Data

(62) Division of application No. 10/053,847, filed on Jan. 22, 2002.

(51) Int. Cl.$^7$ .............................................. C07C 45/50
(52) U.S. Cl. ....................................... 568/451; 568/454
(58) Field of Search .................................. 568/451, 454

(56) References Cited

U.S. PATENT DOCUMENTS

| | | |
|---|---|---|
| 3,239,566 A | 3/1966 | Slaugh et al. |
| 3,527,809 A | 9/1970 | Pruett et al. |
| 4,200,592 A | 4/1980 | Davidson et al. |
| 4,306,086 A | 12/1981 | Demay |
| 4,608,239 A | 8/1986 | Devon |
| 5,756,855 A | 5/1998 | Abatjoglou et al. |
| 5,840,647 A | 11/1998 | Puckette et al. |
| 5,929,289 A | 7/1999 | Abatjoglou et al. |

FOREIGN PATENT DOCUMENTS

| | | |
|---|---|---|
| EP | 0 590 613 A | 4/1994 |
| EP | 0 697 391 | 2/1996 |
| WO | WO 01 51441 A | 7/2001 |

OTHER PUBLICATIONS

Crocker, Christopher et al, "Preparation and Reactions of Some Fluorophosphine Complexes of Palladium, Platinum, and Rhodium", Chemical Abstracts XP002246347 Abstract & Journal of Chemical Research (Synopses) (1981), (2), 36.
Hitchcock, Peter B., "Fluorophosphine Complexes of Rhodium (I) and Iridium(I): Towards the Design of Systems with Extended Metal–Metal Interaction. The Crystal Structure of (IrCI(PF3)2)", Journal of the Chemical Society, 7, 1985, 1295–1301.

*Primary Examiner*—Johann Richter
*Assistant Examiner*—Sikarl A. Witherspoon
(74) *Attorney, Agent, or Firm*—Eric D. Middlemas; Bernard J. Graves, Jr.

(57) ABSTRACT

Disclosed are novel catalyst systems comprising (1) a diorgano fluorophosphite ligand; (2) rhodium, wherein the ratio of gram moles fluorophosphite ligand (1) to gram atoms of rhodium is at least 1:1; and (3) a Group VIII metal, other than rhodium, or Group VIII metal-containing compound, in an amount effective to reduce the formation of HF during the use of the catalyst system. The presence of the other Group VIII metal decreases the amount of hydrogen fluoride produced during the use of the catalyst system. The hydrogen fluoride originates from very low level degradation of the ligand. Also disclosed are novel catalyst solutions of the aforesaid catalyst system and the use of the catalyst system in the hydroformylation of olefins to produce aldehydes.

10 Claims, No Drawings

STABILIZATION OF FLUOROPHOSPHITE-CONTAINING CATALYSTS

CROSS REFERENCES TO RELATED APPLICATIONS

This application is a divisional of prior U.S. application Ser. No. 10/053,847, filed Jan. 22, 2002.

FIELD OF THE INVENTION

The present invention pertains to a novel catalyst system comprising (1) a diorgano fluorophosphite ligand; (2) rhodium; and (3) a Group VII metal, other than rhodium, or Group VII metal-containing compound, in an amount effective to reduce the formation of HF during the use of the catalyst system. The presence of the other Group VII metal decreases the amount of hydrogen fluoride produced during the use of the catalyst system. The hydrogen fluoride originates from very low level degradation of the ligand. The present invention also pertains to catalyst solutions of the aforesaid catalyst system and the use of the catalyst system in the hydroformylation of olefins to produce aldehydes.

BACKGROUND OF THE INVENTION

Homogenous catalyst solutions prepared from transition metals and phosphorus ligands are used widely in the chemical industry. The advantages of homogenous catalysts over heterogeneous catalysts usually include higher reactivity and higher selectivity. However, homogenous catalysts often are subject to degradation and concomitant loss of activity over time. The problem of catalyst degradation is aggravated if the degradation process leads to the formation of unwanted side products that are found as contaminants in the product Therefore, it is highly desirable to develop technologies that extend the effective catalyst lifetime, enhance selectivity and reduce contaminants in the product.

The hydroformylation reaction, also known as the oxo reaction, is used extensively in commercial processes for the preparation of aldehydes by the reaction of one mole of an olefin with one mole each of hydrogen and carbon monoxide. The most extensive use of the reaction is in the preparation of normal- and iso-butyraldehyde from propylene. The ratio of the amounts of the normal to iso aldehyde products typically is referred to as the normal to iso (N:I) or the normal to branched (N:B) ratio. In the case of propylene, the normal- and iso-butyraldehydes obtained from propylene are in turn converted into many commercially-valuable chemical products such as, for example, n-butanol, 2-ethylhexanol, n-butyric acid, iso-butanol, neopentyl glycol, 2,2,4-trimethyl-1,3-pentanediol, the mono-isobutyrate and di-isobutyrate esters of 2,2,4-trimethyl-1,3-propanediol. The hydroformylation of higher α-olefins such as 1-octene, 1-hexene, and 1-decene yield aldehyde products which are useful feedstocks for the preparation of detergent alcohols and plasticizer alcohols. The hydroformylation of substituted olefins such as allyl alcohol is useful for the production of other commercially valuable products such as 1,4-butanediol.

Catalysts used in the hydroformylation reaction typically contain rhodium complexes comprising at least one phosphorus ligand. U.S. Pat. No. 3,239,566, issued Mar. 8, 1966, to Slaugh and Mullineaux, discloses a low pressure hydroformylation process using trialkylphosphines in combination with rhodium catalysts for the preparation of aldehydes. Trialkylphosphines have seen much use in industrial hydroformylation processes but they typically produce a limited range of products and, furthermore, frequently are very oxygen sensitive. U.S. Pat. No. 3,527,809, issued Sep. 8, 1970 to Pruett and Smith, discloses a low pressure hydroformylation process which utilizes triarylphosphine or triarylphosphite ligands in combination with rhodium catalysts. The ligands disclosed by Pruett and Smith, although used in many commercial applications, have limitations due to oxidative and hydrolytic stability problems. Since these early disclosures, numerous improvements have been made to increase the catalyst stability, catalyst activity and the product ratio with a heavy emphasis on yielding linear aldehyde product. A wide variety. of monodentate phosphite and phosphine ligands, bidentate ligands such as bisphosphites and bisphosphines as well as tridentate and polydentate ligands have been prepared and disclosed in the literature. U.S. Pat. No. 5,840,647 discloses the use of diorganofluorophosphites, also known as fluorophosphites, as the phosphorus ligand component of hydroformylation catalysts.

It also is known that the hydroformylation catalysts suffer from the drawback that the phosphorus ligands can be decomposed by a variety of mechanisms including oxidation, acid catalyzed hydrolysis, and, in the case of certain tri-organo phosphite ligands, the rhodium-catalyzed decomposition of the phosphite as disclosed in U.S. Pat. Nos. 5,756,855 and 5,929,289. The ligand decomposition reactions are detrimental to the overall economics of the process as they result in the loss of the valuable ligand and also can result in the formation of ligand degradation products which may act as catalyst poisons. We have found that diorgano fluorophosphite compounds described in U.S. Pat. No. 5,840,647 undergo low level degradation to generate hydrogen fluoride with concomitant loss of ligand. The hydrogen fluoride contaminates the product aldehydes which is highly undesirable as it can lead to corrosion and the formation of by-products.

SUMMARY OF THE INVENTION

The present invention provides a means for the stabilization of certain homogenous catalyst systems comprising at least one diorgano fluorophosphite compound that results in the suppression of the formation of hydrogen fluoride from the catalyst systems. Thus, one embodiment of the present invention is a novel catalyst system comprising (1) a diorgano fluorophosphite ligand; and (3) rhodium; wherein the ratio of gram moles fluorophosphite ligand to gram atoms of rhodium is at least 1:1; and (3) a Group VIII metal, other than rhodium, or Group VIII metal-containing compound, in an amount effective to reduce the formation of HF during the use of the catalyst system, i.e., during the use of the catalyst to catalyze organic processes. The novel catalyst systems may be used in a wide variety of transition metal-catalyzed processes such as, for example, hydroformylation, hydrogenation, isomerization, hydrocyanation, hydrosilation, carbonylations, oxidations, acetoxylations, epoxidations, hydroamination, dihydroxylation, cyclopropanation, telomerizatons, carbon hydrogen bond activation, olefin metathesis, olefin dimerizations, oligomerizations, olefin polymerizations, olefin-carbon monoxide copolymerizations, butadiene dimerization and oligomerization, butadiene polymerization, and other carbon-carbon bond forming reactions such as the Heck reaction and arene coupling reactions. The catalyst systems provided by the present invention are especially useful for the hydroformylation of olefins to produce aldehydes.

A second embodiment of our invention concerns a novel catalyst solution comprising (1) one or more diorgano fluorophosphite ligands, (2) rhodium, (3) a Group VIII metal, other than rhodium, or Group Vil metal-containing compound, in an amount effective to reduce the formation of HF, and (4) a hydroformylation solvent. This embodiment comprises a solution of the active catalyst in which a carbonylation process such as the hydroformylation of an ethylenically-unsaturated compound may be carried out.

A third embodiment of the present invention pertains to a hydroformylation process utilizing the above-described catalyst systems and solutions. The process of the present invention therefore includes a process for preparing an aldehyde which comprises contacting an olefin, hydrogen and carbon monoxide with a solution of a catalyst system comprising and (1) a diorgano fluorophosphite ligand, (2) rhodium and (3) a Group VII metal, other than rhodium, or Group Vil metal-containing compound, in an amount effective to reduce the formation of HF, wherein the ratio of gram moles fluorophosphite ligand to gram atoms of rhodium is at least 1:1.

DETAILED DESCRIPTION OF THE INVENTION

The diorgano or dihydrocarbyl fluorophosphite component of the catalyst of the present invention is a trivalent phosphorus compound in which the phosphorus atom is bonded to two oxygen atoms and one fluorine atom. The oxygen atoms are further attached to organic groups which be aromatic or alkyl groups. The organic groups may be independent groups or may be joined together in cyclic or polymeric structures. The fluorophosphite compounds or ligands are represented by formula (I):

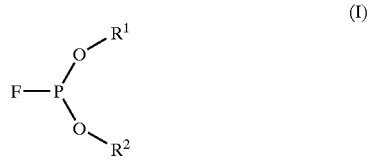

(I)

wherein $R^1$ and $R^2$ represent the same or different hydrocarbyl groups or RI and $R^2$ may in combination represent joined groups constituting a hydrocarbylene group which, with the phosphite residue, forms a cyclic ligand compound. The hydrocarbyl and joined hydrocarbyl groups represented by $R^1$ and $R^2$ may be selected, for example, from the same or different unsubstituted and substituted alkyl, cycloalkyl and aryl groups containing a total of up to about 40 carbon atoms. The total carbon content of substituents $R^1$ and $R^2$ preferably is in the range of about 12 to 35 carbon atoms. Examples of the alkyl groups which $R^1$ and/or $R^2$ separately or individually can represent include ethyl, butyl, pentyl, hexyl, 2-ethylhexyl, octyl, decyl, dodecyl, octadecyl and various isomers thereof. The alkyl groups may be substituted, for example, with up to two substituents such as alkoxy, cycloalkoxy, formyl, alkanoyl, cycloalkyl, aryl, aryloxy, aroyl, carboxyl, carboxylate salts, alkoxycarbonyl, alkanoyloxy, cyano, sulfonic acid, sulfonate salts and the like. Cyclopentyl, cyclohexyl and cycloheptyl are examples of the cycloalkyl groups $R^1$ and/or $R^2$ individually can represent. The cycloalkyl groups may be substituted with alkyl or any of the substituents described with respect to the possible substituted alkyl groups. The alkyl and cycloalkyl groups which $R^1$ and/or $R^2$ individually can represent preferably are alkyl of up to about 8 carbon atoms, benzyl, cyclopentyl, cyclohexyl or cycloheptyl.

Examples of the aryl groups which $R^1$ and/or $R^2$ individually can represent include carbocyclic aryl such as phenyl, naphthyl, anthracenyl and substituted derivatives thereof. Examples of the carbocyclic aryl groups which $R^1$ and/or $R^2$ individually can represent are the radicals having the formulas

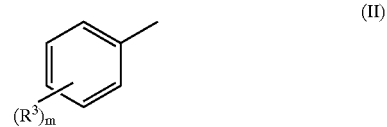

(II)

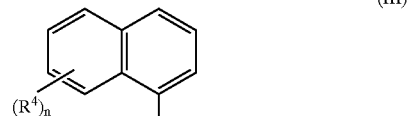

(III)

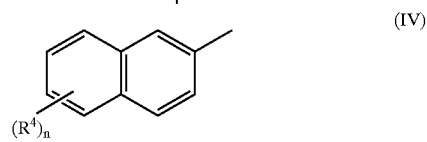

(IV)

wherein $R^3$ and $R^4$ may represent one or more substituents independently selected from alkyl, alkoxy, halogen, cycloalkoxy, formyl, alkanoyl, cycloalkyl, aryl, aryloxy, aroyl, carboxyl, carboxylate salts, alkoxycarbonyl, alkanoyloxy, cyano, sulfonic acid, sulfonate salts and the like. The alkyl moiety of the aforesaid alkyl, alkoxy, alkanoyl, alkoxycarbonyl and alkanoyloxy groups typically contain up to about 8 carbon atoms. Although it is possible for m to represent 0 to 5 and for n to represent 0 to 7, the value of each of m and n usually will not exceed 2. $R^3$ and $R^4$ preferably represent halogens and/or lower alkyl groups, i.e., straight-chain and branched-chain alkyl of up to about 4 carbon atoms, and m and n each represent 0, 1 or 2.

Alternatively, $R^1$ and $R^2$ in combination or collectively may represent a divalent arylene group. The divalent groups which $R^1$ and $R^2$ collectively may represent include radicals having the formula

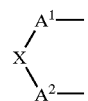

wherein
each of $A^1$ and $A^2$ is an arylene radical, e.g., a divalent, carbocyclic aromatic group containing 6 to 10 ring carbon atoms, wherein each ester oxygen atom of fluorophosphite (I) is bonded to a ring carbon atom of $A^1$ and $A^2$;
X is (i) a chemical bond directly between ring carbon atoms of $A^1$ and $A^2$ or (ii) an oxygen atom, a group having the formula —$(CH_2)_y$— wherein y is 2 to 4 or a group having the formula

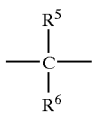

wherein $R^5$ is hydrogen, alkyl or aryl, e.g., the aryl groups illustrated by formulas (II), (III) and (IV), and $R^6$ is hydrogen or alkyl. The total carbon content of the group —$C(R^5)(R^6)$— normally will not exceed 20 and, preferably, is in the range of 1 to 8 carbon atoms. Normally, when $R^1$ and $R^2$ collectively represent a divalent hydrocarbylene group, the fluorophosphite ester oxygen atoms, i.e. the oxygen atoms depicted in formula (I), are separated by a chain of atoms containing at least 3 carbon atoms.

Examples of the arylene groups represented by each of $A^1$ and $A^2$ include the divalent radicals represented by the formulas (V), (IV) and (VII).

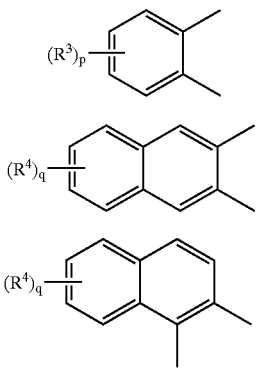

(V)

(VI)

(VII)

wherein $R^3$ and $R^4$ may represent one or more substituents independently selected from alkyl, alkoxy, halogen, cycloalkoxy, formyl, alkanoyl, cycloalkyl, aryl, aryloxy, aroyl, carboxyl, carboxylate salts, alkoxycarbonyl, alkanoyloxy, cyano, sulfonic acid, sulfonate salts and the like. The alkyl moiety of such alkyl, alkoxy, alkanoyl, alkoxycarbonyl and alkanoyloxy groups typically contains up to about 8 carbon atoms. Although it is possible for p to represent 0 to 4 and for q to represent 0 to 6, the value of each of p and q usually will not exceed 2. $R^3$ and $R^4$ preferably represent a halogen such as chlorine, a lower alkyl group, i.e., straight-chain and branched-chain alkyl of up to about 4 carbon atoms, or lower alkoxy; and p and q each represent 0, 1 or 2.

The dihydrocarbyl fluorophosphite compounds that are most preferred, e.g., those which exhibit the best stability, are those wherein the fluorophosphite oxygen atoms are bonded directly to a ring carbon atom of a carbocyclic, aromatic group, e.g., an aryl or arylene group represented by any of formulas (II) through (VII). When $R^1$ and $R^2$ individually each represents an aryl radical, e.g., a phenyl group, it is further preferred that 1 or both of the ring carbon atoms that are in a position ortho to the ring carbon atoms bonded to the fluorophosphite ester oxygen atom are substituted with an alkyl group, especially a branched chain alkyl group such as isopropyl, tert-butyl, tert-octyl and the like. Similarly, when $R^1$ and $R^2$ collectively represent a radical having the formula

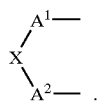

the ring carbon atoms of arylene radicals $A^1$ and $A^2$ that are in a position ortho to the ring carbon atoms bonded to the fluorophosphite ester oxygen atom are substituted with an alkyl group, preferably a branched chain alkyl group such as isopropyl, tertbutyl, tert-octyl and the like.

The most preferred dihydrocarbyl fluorophosphite compounds have the general formula:

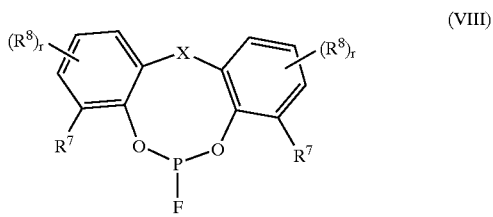

(VIII)

wherein $R^7$ represents hydrogen, halogen such as chloro or $C_1$ to $C_{12}$ alkyl, preferably $C_1$ to $C_4$ alkyl; $R^8$ represent halogen such as chloro, $C_1$ to $C_{12}$ alkyl, preferably $C_1$ to $C_4$ alkyl, or $C_1$ to $C_{12}$ alkoxy, preferably $C_1$ to $C_4$ alkoxy; r is 0, 1 or 2; and X is (i) a chemical bond directly between ring carbon atoms of the arylene groups or (ii) a group having the formula

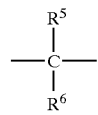

wherein $R^5$ is hydrogen, alkyl or aryl, e.g., the aryl groups illustrated by formulas (II), (III) and (IV), and $R^8$ is hydrogen or alkyl.

Specific illustrative examples of the phosphite ligands employable in the present invention within the scope of generic formulas I–III above include the following phosphite compounds:

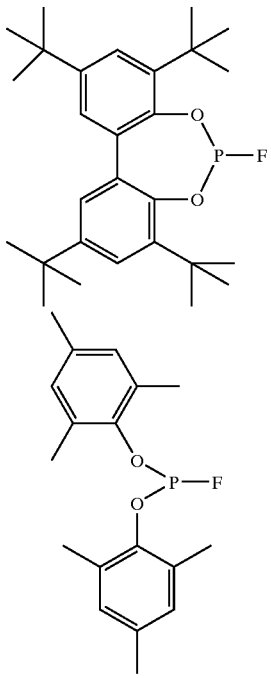

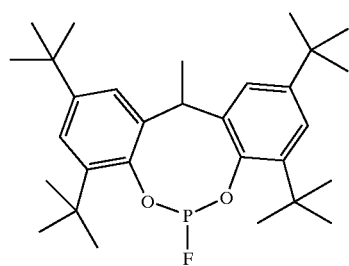
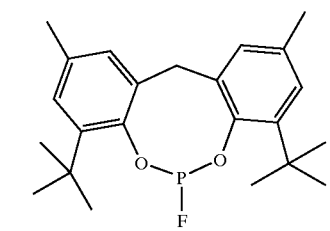
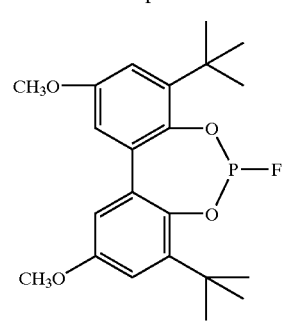
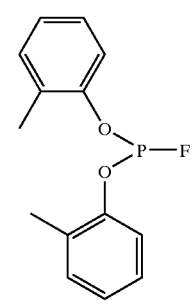
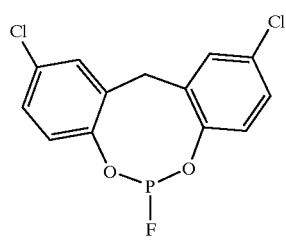
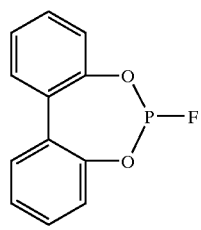
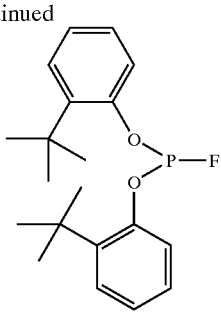
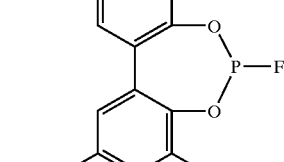
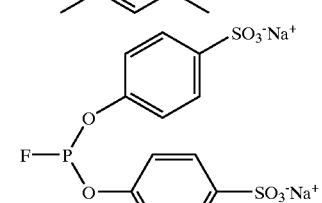
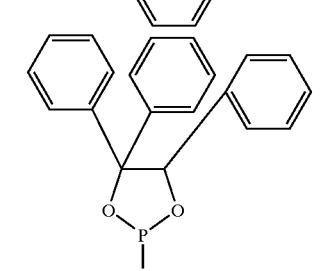
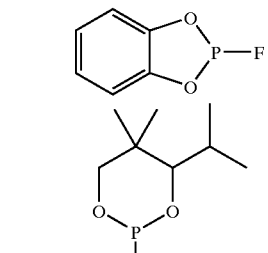
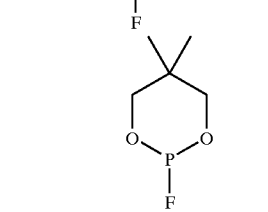
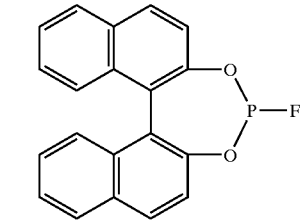

The novel catalyst systems provided by the present invention comprise a combination of (a) one or more of the dihydrocarbyl fluorophosphite compounds described in detail hereinabove; (b) rhodium; and (c) a Group VIII metal, other than rhodium, or Group VIII metal-containing compound. The rhodium metal may be provided in the form of various metal compounds such as rhodium carboxylate salts. Rhodium compounds that may be used as a source of rhodium for the active catalyst include rhodium II or rhodium III salts of carboxylic acids, examples of which include di-rhodium tetraacetate dihydrate, rhodium(II) acetate, rhodium(II) isobutyrate, rhodium(II) 2-ethylhexanoate, rhodium(II) benzoate and rhodium(II) octanoate. Also, rhodium carbonyl species such as $Rh_4(CO)_{12}$, $Rh_6(CO)_{16}$ and rhodium(I) acetylacetonate dicarbonyl may be suitable rhodium sources. Additionally, rhodium organophosphine complexes such as tris(triphenylphosphine) rhodium carbonyl hydride may be used when the phosphine moieties of the complex fed are easily displaced by the fluorophosphite ligands of the present invention. Less desirable rhodium sources are rhodium salts of strong mineral acids such as chlorides, bromides, nitrates, sulfates, phosphates and the like. We have found rhodium 2-ethylhexanoate to be a particularly preferred source of rhodium from which to prepare the complex catalyst of the invention because it is a convenient source of soluble rhodium, as it can be efficiently prepared from inorganic rhodium salts such as rhodium halides.

The ratio of gram moles dihydrocarbyl fluorophosphite ligand to gram atoms rhodium normally is at least 1:1 and can vary over a wide range, e.g., gram mole fluorophosphite:gram atom transition metal ratios of about 1:1 to 500:1. The gram mole fluorophosphite:gram atom rhodium ratio preferably is in the range of about 5:1 up to 150:1 with ratios in the range of about 5:1 to 100;1 being particularly preferred.

The amount of the stabilizer Group VIII metal, i.e., the Group VIII metal other than rhodium ("other Group VIII metal"), present in the novel catalyst systems provided by the present invention typically should provide up to a 10-fold gram atom excess of the other Group VIII metal based on the gram atoms of rhodium present in the catalyst system. Preferably, the gram atom ratio of the other Group VIII metal:rhodium metal is in the range of about 1:1 to 5:1. In the practice of the present invention, the other Group VIII metal may be introduced to the catalyst precursor materials or directly into the hydroformylation reactor in the form of stable precursor compounds. Examples of stable precursor compounds are the carbonyls, carboxylates, oxides, acetonylacetonates and phosphates of the other Group VIII metals. The preferred Group VIII metals for use as stabilizers are platinum, cobalt, ruthenium and palladium. Normally, the precursor of the other Group VIII metal will not contain any known catalyst poisons such as sulfur or inorganic halides. The metal stabilizer precursor compounds may be added to the hydroformylation reaction mixture as a single batch as a component of the overall catalyst or in small quantities over an extended period of time. Furthermore, if the concentration of the other Group VIII metal stabilizer should decrease over time, additional Group VIII metal stabilizer may be added during the hydroformylation process to maintain the stabilizer at an effective level in the process.

A second embodiment of our invention concerns a novel catalyst solution comprising (a) one or more of the fluorophosphite ligands of formula (I), (b) rhodium, (c) a Group VIII metal, other than rhodium, or Group VIII metal-containing compound and (d) a hydroformylation solvent. This embodiment comprises a solution of the active catalyst in which a carbonylation process such as the hydroformylation of an ethylenically-unsaturated compound may be carried out.

The hydroformylation reaction solvent may be selected from a wide variety of compounds, mixture of compounds, or materials that are liquid at the pressure at which the process is being operated, do not affect adversely the hydroformylation process, and are inert with respect to the catalyst, olefin, hydrogen and carbon monoxide. Such compounds and materials include various alkanes, cycloalkanes, alkenes, cycloalkenes, carbocyclic aromatic compounds, alcohols, esters, ketones, acetals, ethers and water. Specific examples of such solvents include alkane and cycloalkanes such as dodecane, decalin, octane, iso-octane mixtures, cyclohexane, cyclooctane, cyclododecane, methylcyclohexane; aromatic hydrocarbons such as benzene, toluene, xylene isomers, tetralin, cumene, alkyl-substituted aromatic compounds such as the isomers of diisopropylbenzene, triisopropylbenzene and tert-butylbenzene; alkenes and cycloalkenes such as 1,7-octadiene, dicyclopentadiene, 1,5-cyclooctadiene, octene-1, octene-2,4vinylcyclohexene, cyclohexene, 1,5,9-cyclododecatriene, 1-pentene; crude hydrocarbon mixtures such as naphtha, mineral oils and kerosene;. high-boiling esters such as 2,2,4-trimethyl-1,3-pentanediol mono- and di-isobutyrate and dioctyl phthalate; hydrogenated polydecenes, e.g., materials marketed under the tradenames Durasynl 70 and Durasyn 180; and epoxidized soybean oil. The aldehyde product of the hydroformylation process also may be used. In practice, the preferred solvent is the higher boiling by-products that are naturally formed during the process of the hydroformylation reaction and the subsequent steps, e.g., distillations, that are required for aldehyde product isolation. The main criteria for the solvent is that it dissolves the catalyst and olefin substrate and does not act as a poison to the catalyst. Preferred solvents for the production of volatile aldehydes, e.g., propionaldehyde and the butyraldehydes, are those that are sufficiently high boiling to remain, for the most part, in a gas sparged reactor. Solvents and solvent combinations that are preferred for use in the production of less volatile and non-volatile aldehyde products include 1-methyl-2-pyrrolidinone, dimethylformamide, perfluorinated solvents such as perfluorokerosene, sulfolane, water, and high boiling hydrocarbon liquids as well as combinations of these solvents. We have found that non-hydroxylic compounds, in general, and hydrocarbons, in particular, may be used advantageously as the hydroformylation solvent since their use can minimize decomposition of the fluorophosphite ester ligands.

The concentration of the rhodium, ligand and other Group VIII metal in the hydroformylation solvent or reaction mixture is not critical for the successful operation of our invention. As mentioned hereinabove, a gram mole ligand:gram atom rhodium ratio of at least 1:1 normally is maintained in the reaction mixture and the gram atom ratio of the other Group VIII metal:rhodium metal preferably is in the range of about 1:1 to 5:1. The absolute concentration of rhodium in the reaction mixture or solution may vary from 1 mg/liter up to 5000 mg/liter or more. When the process is operated within the practical conditions of this invention, the. concentration of rhodium in the reaction solution normally is in the range of about 20 to 300 mg/liter. Concentrations of rhodium lower than this range generally do not yield acceptable reaction rates with most olefin reactants and/or require reactor operating temperatures that are so high as to be detrimental to catalyst stability. Higher rhodium concentrations are not preferred because of the high cost of rhodium. The concentration of the dihydrocarbyl fluorophosphite ligand in the hydroformylation solvent or reaction mixture typically is between about 0.005 and 15 weight percent based on the total weight of the reaction mixture. More typically, the ligand concentration is between 0.001 and 10 weight percent, and preferably is between about 0.05 and 5 weight percent on that basis.

No special or unusual techniques are required for preparing the catalyst systems and solutions of the present invention, although it is preferred, to obtain a catalyst of high activity, that all manipulations of the rhodium and fluorophosphite ligand components be carried out under an inert atmosphere, e.g., nitrogen, argon and the like. The desired quantities of a suitable rhodium compound, ligand and an other Group VIII compound are charged to the reactor in a suitable solvent. The sequence in which the various catalyst components or reactants are charged to the reactor is not critical.

The reaction mixtures used in the process of the present invention are comprised of (a) one or more of the dihydrocarbyl fluorophosphite compounds described in detail hereinabove; (b) rhodium; and (c) a Group VIII metal, other than rhodium, or Group VIII metal-containing compound. The rhodium functions as a hydroformylation catalyst in the form of a complex catalyst which is formed in situ from the rhodium, carbon monoxide, the dihydrocarbyl fluorophosphite ligand and hydrogen. Additional components, such as the olefin, may also be bonded to the rhodium at various points in the catalytic cycle. The rhodium catalyst and catalytic precursor compounds are preferably free of any poisons such as sulfur compounds, inorganic chlorides and bromides or readily hydrolyzable organic halogen compounds. The reactants and catalyst components should also be free of any materials that will promote by-product formation from the product aldehyde. Materials known to promote by-product formation from the product aldehyde include iron compounds, strong acids or bases, and amines.

The third embodiment of the present invention pertains to a hydroformylation process utilizing the above-described catalyst systems and solutions. The process of the present invention therefore is a process for preparing an aldehyde which comprises contacting an olefin, hydrogen and carbon monoxide with a solution of a catalyst system comprising (1) one or more of the above-described dihydrocarbyl fluorophosphite compounds; (2) rhodium; and (3) a Group VIII metal, other than rhodium, or Group VIII metal-containing compound, wherein the ratio of gram moles ligand:gram atom rhodium is at least 1:1. The olefins that may be hydroformylated by means of our novel process comprise aliphatic, including ethylenically-unsaturated, low molecular weight polymers, alicyclic, aromatic and heterocyclic mono-, di- and tri-olefins containing up to about 40 carbon atoms. Examples of the aliphatic olefins that may be utilized in the process include straight- and branched-chain, unsubstituted and substituted, aliphatic mono-α-olefins containing up to about 20 carbon atoms. Examples of the groups that may be present on the substituted mono-α-olefins include hydroxy; alkoxy including ethers and acetals; alkanoyloxy such as acetoxy; amino including substituted amino; carboxy; alkoxycarbonyl; carboxamido; keto; cyano; and the like. Preferred aliphatic mono-α-olefins have the general formulas:

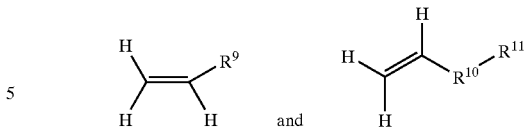

wherein
$R^9$ is hydrogen or straight- or branched-chain alkyl of up to about 8 carbon atoms;
$R^{10}$ is straight- or branched-chain alkylene of up to about 18 carbon atoms; and
$R^{11}$ is hydroxy, alkoxy of up to about 4 carbon atoms, alkanoyloxy of up to about 4 carbon atoms, carboxyl or alkoxycarbonyl of 2 to about 10 carbon atoms.

Specific examples of the aliphatic mono-α-olefins include ethylene, propylene, 1-butene, 1-octene, allyl alcohol and 3-acetoxy-1-propene.

The aliphatic, di-olefins may contain up to about 40 carbon atoms. Preferred aliphatic, di-olefins have the general formula:

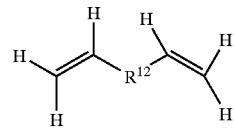

wherein $R^{12}$ is straight- or branched-chain alkylene having 1 to about 18 carbon atoms.

The cyclic olefins which may be used in the hydroformylation process of the present invention may be cycloalkenes, e.g., cyclohexene, 1,5-cyclooctadiene, and cyclodecatriene, and from various vinyl-substituted cycloalkanes, cycloalkenes, heterocyclic and aromatic compounds. Examples of such cyclic olefins include 4-vinylcyclohexene, 1,3-cyclo-hexadiene, 4cyclohexene-carboxylic acid, methyl 4-cyclohexene-carboxylic acid, 1,4-cyclooctadiene and 1,5, 9cyclododecatriene.

Mixtures of olefins also can be used in the practice of this invention. The mixtures may be of the same carbon number such as mixtures of n-octenes or it may represent refinery distillation cuts which will contain a mixture of olefins over a range of several carbon numbers.

The olefin reactants which are particularly preferred comprise mono-α-olefins of 2 to 10 carbon atoms, especially propylene.

The reaction conditions used are not critical for the operation of the process and conventional hydroformylation conditions normally are used. The process requires that an olefin is contacted with hydrogen and carbon monoxide in the presence of the novel catalyst system described hereinabove. While the process may be carried out at temperatures in the range of about 20 to 200° C., the preferred hydroformylation reaction temperatures are from about 50 to 150° C. with the most favored reaction temperatures ranging from about 80 to 130° C. Higher reactor temperatures are not favored because of increased rates of catalyst decomposition while lower reactor temperatures result in relatively slow reaction rates.

The hydroformylation process of the present invention normally is carried out at elevated pressures in the range of about 0.7 to 69 bars gauge (barg; about 10 to 1000 pounds per square inch—psig), preferably in the range of about 6.9 to 27.6 barg (about 100 to 400 psig). Lower pressures result in the rate of reaction being economically unattractive whereas higher pressures, e.g., greater than 69 barg, result in increased gas compression and equipment costs. In the present invention, the synthesis gas, i.e., CO and $H_2$, is introduced into the reactor in a continuous manner by means, for example, of a compressor. The partial pressures of the ratio of the hydrogen to carbon monoxide in the feed is selected according to the desired linear to branched isomer ratio in the product. Generally, the partial pressure of hydrogen and carbon monoxide in the reactor is maintained within the range of about 0.4 to 13 barg (about 5 to 188 psig) for each gas. The partial pressure of carbon monoxide in the reactor is maintained within the range of about 0.4 to 13 barg (about 5 to 188 psig) and is varied independently of the hydrogen partial pressure.

The molar ratio of hydrogen to carbon monoxide can be varied widely within these partial pressure ranges for the hydrogen and carbon monoxide. The ratios of the hydrogen to carbon monoxide and the partial pressure of each in the synthesis gas can be readily changed by the addition of either hydrogen or carbon monoxide to the synthesis gas stream. We have found that with the dihydrocarbyl fluorophosphite ligands present in the catalyst of the present invention, the ratio of linear to branched products can be varied widely by changing the partial pressures of the carbon monoxide in the reactor. For example, the hydrogen:carbon monoxide mole ratio in the reactor may vary from about 10:1 to 1:10.

The amount of olefin present in the reaction mixture also is not critical. For example, relatively high-boiling olefins such as 1-octene may function both as the olefin reactant and the process solvent. In the hydroformylation of a gaseous olefin feedstock such as propylene, the partial pressures in the vapor space in the reactor typically are in the range of about 0.01 to 34 barg. In practice the rate of reaction is favored by high concentrations of olefin in the reactor. In the hydroformylation of propylene, the partial pressure of propylene preferably is greater than 0.4 barg, e.g., from about 0.4 to 9 barg. In the case of ethylene hydroformylation, the preferred partial pressure of ethylene in the reactor is greater than 0.01 barg.

Any of the known hydroformylation reactor designs or configurations may be used in carrying out the process provided by the present invention. Thus, a gas-sparged, vapor take-off reactor design as disclosed in the examples set forth herein may be used. In this mode of operation the catalyst which is dissolved in a high boiling organic solvent under pressure does not leave the reaction zone with the aldehyde product which is taken overhead by the unreacted gases. The overhead gases then are chilled in a vapor/liquid separator to liquify the aldehyde product and the gases can be recycled to the reactor. The liquid product is let down to atmospheric pressure for separation and purification by conventional technique. The process also may be practiced in a batchwise manner by contacting the olefin, hydrogen and carbon monoxide with the present catalyst in an autoclave.

A reactor design where catalyst and feedstock are pumped into a reactor and allowed to overflow with product aldehyde, i.e. liquid overflow reactor design, is also suitable. For example, high boiling aldehyde products such as nonyl aldehydes may be prepared in a continuous manner with the aldehyde product being removed from the reactor zone as a liquid in combination with the catalyst. The aldehyde product may be separated from the catalyst by conventional means such as by distillation or extraction and the catalyst then recycled back to the reactor. Water soluble aldehyde products, such as hydroxy butyraldehyde products obtained by the hydroformylation of allyl alcohol, can be separated from the catalyst by extraction techniques. A trickle-bed reactor design also is suitable for this process. It will be apparent to those skilled in the art that other reactor schemes may be used with this invention.

The other Group VIII metal present in the catalyst compositions of the present invention reduces the generation of the hydrogen fluoride by increasing the stability of the catalyst components. When the catalyst is stabilized against degradation, less hydrogen fluoride is generated and less hydrogen fluoride is found in the reaction product. The stabilization factor is best illustrated in data from a continuous hydroformylation bench unit used to prepare butyraldehydes. For example, in the absence of an other Group VIII metal, the hourly products of the bench unit runs will contain about 0.10 milligrams of hydrogen fluoride per 100 grams of butyraldehyde. The addition of the other Group VIII metal reduces the amount of hydrogen. fluoride measured in the aldehyde, often as much as thirty percent or more as shown by the examples set forth below. Thus, a further embodiment of our invention provides a method for reducing the amount of HF formed in a hydroformylation reaction utilizing rhodium-fluorophosphite catalyst complexes as catalyst, which comprises charging the reaction vessel with an HF-reducing effective amount of an other Group VIII compound.

EXAMPLES

The various embodiments of the present invention are further illustrated by the following examples. The hydroformylation process in which propylene is hydroformylated to produce butyraldehydes is carried out in a vapor take-off reactor consisting of a vertically arranged stainless steel pipe having a 2.5 cm inside diameter and a length of 1.2 meters. The reactor is encased in an external jacket that is connected to a hot oil machine. The reactor has a filter element welded into the side down near the bottom of the reactor for the inlet of gaseous reactants. The reactor contains a thermowell which is arranged axially with the reactor in its center for accurate measurement of the temperature of the hydroformylation reaction mixture. The bottom of the reactor has a high pressure tubing connection that is connected to a cross. One of the connections to the cross permits the addition of nongaseous reactants such as octene-1 or make-up solvent, another leads to the high-pressure connection of a differential pressure (D/P) cell that is used to measure catalyst level in the reactor and the bottom connection is used for draining the catalyst solution at the end of the run.

In the hydroformylation of propylene in a vapor take-off mode of operation, the hydroformylation reaction mixture or solution containing the catalyst is sparged under pressure with the incoming reactants of propylene, hydrogen and carbon monoxide as well as any inert feed such as nitrogen. As butyraldehyde is formed in the catalyst solution, it and unreacted reactant gases are removed as a vapor from the top of the reactor by a side-port. The vapor removed is chilled in a high-pressure separator where the butyraldehyde product is condensed along with some of the unreacted propylene. The uncondensed gases are let down to atmospheric pressure via the pressure control valve. These gases pass through a series of dry-ice traps where any other aldehyde product is collected. The product from the high-pressure separator is combined with that of the traps, and is subsequently weighed and analyzed by standard gas/liquid phase chromatography (GLC) techniques for the net weight and normal/iso ratio of the butyraldehyde product.

The gaseous feeds to the reactor are fed to the reactor via twin cylinder manifolds and high-pressure regulators. The hydrogen passes through a mass flow controller and then through a commercially available "Deoxo" (registered trademark of Engelhard Inc.) catalyst bed to remove any oxygen contamination. The carbon monoxide passes through an iron carbonyl removal bed (as disclosed in U.S. Pat. No. 4,608,239), a similar "Deoxo" bed heated to 125° C., and then a mass flow contoller. Nitrogen can be added to the feed mixture as an inert gas. Nitrogen, when added, is metered in and then mixed with the hydrogen feed prior to the hydrogen Deoxo bed. Propylene is fed to the reactor from feed tanks that are pressurized with hydrogen and is controlled using a liquid mass flow meter. All gases and propylene are passed through a preheater to insure complete vaporization of the liquid propylene prior to entering the reactor.

Fluoride measurements were made with a fluoride ion selective electrode (Orion Research Inc. product 9609BN) in combination with a Metrohm 751 GPD Titrino unit. All measurements, separations and dilutions were carried out in plastic laboratory equipment. All samples analyzed for fluoride content were collected and held in plastic containers. A measured portion of the product aldehyde (20 ml) was extracted with an equal volume (20 ml) of a constant ion strength buffer such as TISAB II (Total Ion Strength Adjustment Buffer) with 1,2 cyclohexane diamine tetraacetic acid—CDTA (a product of Orion Research, Inc.), the aqueous extract diluted with an equal volume of deionized water (20 ml), and the conductivity of the solution was measured and compared to a previously prepared calibration curve.

Comparative Example 1

A comparison bench unit experiment without an added other Group VIII metal was conducted by preparing a catalyst composed of 4.25 grams of a dihydrocarbyl fluorophosphites having the formula:

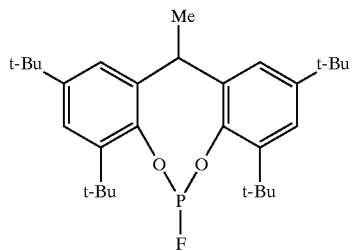

(t-Bu=tertiary butyl, Me=methyl) with 7.5 milligrams of rhodium (as rhodium 2-ethylhexanoate) in 190 milliliters of dioctylphthalate. The mixture was stirred and heated under nitrogen until a homogenous mixture was obtained. The mixture was charged to the reactor described previously and the reactor sealed. The reactor pressure control was set at 17.9 barg (260 psig) and the external oil jacket on the reactor was heated to 105° C. Hydrogen, carbon monoxide, nitrogen and propylene vapors were fed through the frit at the base of the reactor and the reactor allowed to build pressure. The hydrogen and carbon monoxide were fed to the reactor at a rate of 3.35 standard liters per minute. The nitrogen feed was set at 1.0 standard liter per minute. The propylene was metered as a liquid and fed at a rate of 212 grams per hour. The temperature of the external oil was modified to maintain an internal reactor temperature of 115° C. The unit was operated for 5 hours and hourly samples taken. The hourly samples were analyzed as described above and the fluoride content determined. The fluoride content was found to consistently be about 0.105 milligrams of hydrogen fluoride per 100 grams of butyraldehyde.

Example 1–7

The experimental procedure of Example 1 was repeated except that another Group VIII was added to the catalyst mixture. The results of these experiments are tabulated in the Table below which specified the Group VIII metal compound and the amount thereof used in each of Examples 1–7 and wherein Acac is acetylacetonate and Hydrogen Fluoride Content refers to the milligram HF per 100 grams of butyraldehydes produced. The results clearly show that the presence of the additional Group VIII metal compound to the catalyst reduces the amount of hydrogen fluoride in the product aldehyde.

TABLE

| Example Number | Group VIII Metal Compound | Amount Added | Hydrogen Fluoride Content |
|---|---|---|---|
| 2 | Ru(Acac)$_3$ | 0.03 g | 0.046 |
| 3 | Ru(Acac)$_3$ | 0.15 g | 0.047 |
| 4 | Co(Acac)$_3$ | 0.02 g | 0.033 |
| 5 | Pd(acetate)$_2$ | 0.02 g | 0.056 |
| 6 | Co(Acac)$_3$ | 0.10 g | 0.035 |
| 7 | Pt(Acac)$_3$ | 0.03 g | 0.018 |
| 8 | Ru$_3$(CO)$_{12}$ | 0.05 g | 0.045 |

The invention has been described in detail with particular reference to preferred embodiments thereof, but it will be understood that variations and modifications will be effected within the spirit and scope of the invention.

We claim:

1. A process for preparing an aldehyde which comprises contacting an olefin, hydrogen and carbon monoxide with a solution of a catalyst system comprising (1) one or more dihydrocarbyl fluorophosphite ligands having the formula

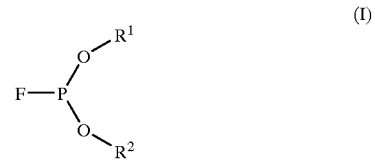

wherein $R^1$ and $R^2$ are aromatic hydrocarbyl radicals which contain a total of up to 40 carbon atoms; (2) rhodium, wherein the ratio of gram moles fluorophosphite ligand to gram atoms rhodium is at least 1:1; (3) a Group VIII metal or Group VIII metal-containing compound in an amount effective to reduce the formation of HF during the process, wherein the Group VIII metal or Group VIII metal-containing compound does not contain rhodium; and (4) a hydroformylation solvent.

2. The process according to claim 1 wherein the concentration of rhodium in the solution is in the range of about 30 to 300 mg per liter; the process is carried out at a temperature of about 50 to 135° C. and a pressure in the range of 0.7 to 69 bars gauge; and the Group VIII metal is platinum, cobalt, ruthenium or palladium.

3. The process according to claim 1 wherein the concentration of rhodium in the solution is in the range of about 50 to 300 mg per liter; the process is carried out at a temperature of about 50 to 135° C. and a at a pressure in the range of 0.7 to 69 bars gauge; $R^1$ and $R^2$ aryl groups independently selected from the group consisting of:

(II)

(III)

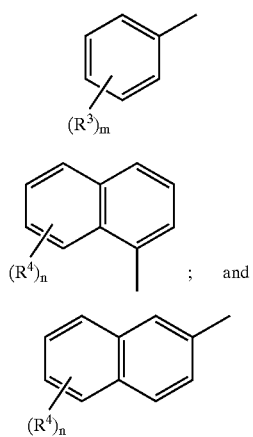

; and (IV)

wherein R³ and R⁴ are independently selected from the group consisting of alkyl, alkoxy, halogen, cycloalkoxy, formyl, alkanoyl, cycloalkyl, aryl, aryloxy, aroyl, carboxyl, carboxylate salts, alkoxycarbonyl, alkanoyloxy, cyano, sulfonic acid and sulfonate salts in which the alkyl moiety of said alkyl, alkoxy, alkanoyl, alkoxycarbonyl and alkanoyloxy groups contains up to 8 carbon atoms; m and n each is 0, 1 or 2; and the ratio of gram moles dihydrocarbyl fluorophosphite ligand to gram atoms rhodium is about 1:1 to 500:1; and the Group VIII metal is selected from the group consisting of platinum, cobalt, ruthenium, and palladium, wherein the gram atom ratio of the Group VIII metal:rhodium metal is in the range of about 1:1 to 5:1.

4. The process according to claim 1 wherein the olefin is a mono-α-olefin of 2 to 10 carbon atoms.

5. The process according to claim 3 wherein the olefin is a mono-α-olefin of 2 to 10 carbon atoms.

6. The process according to claim 1 wherein the concentration of rhodium in the solution is in the range of about 30 to 300 mg per liter; the process is carried out at a temperature of about 50 to 135° C. and a at a pressure in the range of 0.7 to 69 bars gauge; R¹ and R² collectively represent a divalent aromatic hydro-carbylene group containing 12 to 36 carbon atoms; and the Group VIII metal is selected from the group consisting of platinum, cobalt, ruthenium, and palladium.

7. The process according to claim 6 wherein the ratio of gram moles dihydrocarbyl fluorophosphite ligand to gram atoms rhodium is about 1:1 to 500:1 and R¹ and R² collectively represent an arylene group having the formula (V)

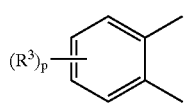

(VI)

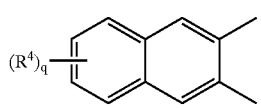

(VII)

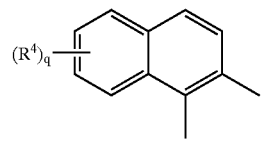

or a radical having the formula

wherein
each of A² and A² is an arylene radical having formula (V), (VI) or (VII) above wherein each ester oxygen atom of fluorophosphite (I) is bonded to a ring carbon atom of A¹ and A²;
X is (i) a chemical bond directly between ring carbon atoms of A¹ and A²; or (ii) an oxygen atom, a group having the formula —(CH$_2$)$_y$— wherein y is 2 to 4, or a group having the formula

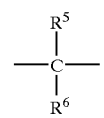

wherein R⁵ is hydrogen, alkyl or aryl; R⁶ is hydrogen or alkyl; and the group —C(R⁵)(R⁶)— contains up to 8 carbon atoms; and wherein R³ and R⁴ are independently selected from the group consisting of alkyl, alkoxy, halogen, cycloalkoxy, formyl, alkanoyl, cycloalkyl, aryl, aryloxy, aroyl, carboxyl, carboxylate salts, alkoxycarbonyl, alkanoyloxy, cyano, sulfonic acid, and sulfonate salts in which the alkyl moiety of said alkyl, alkoxy, alkanoyl, alkoxycarbonyl and alkanoyloxy groups contains up to 8 carbon atoms; p and q each is 0, 1 or 2.

8. The process according to claim 7 wherein the dihydrocarbyl fluorophosphite ligand has the formula (VIII)

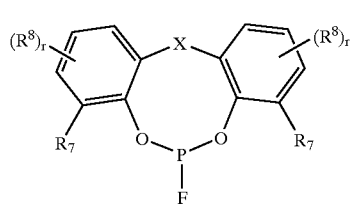

wherein R⁷ represents hydrogen, halogen or C$_1$ to C$_{12}$ alkyl; R⁸ represents halogen, C$_1$ to C$_{12}$ alkyl or C$_1$ to C$_{12}$ alkoxy; r is 0, 1 or 2; and X is a group having the formula

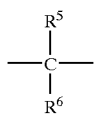

wherein $R^5$ is hydrogen, alkyl or aryl; and $R^6$ is hydrogen or alkyl.

9. A process for preparing an aldehyde which comprises contacting an olefin, hydrogen and carbon monoxide with a solution of a catalyst system comprising (1) a dihydrocarbyl fluorophosphite ligand of the formula

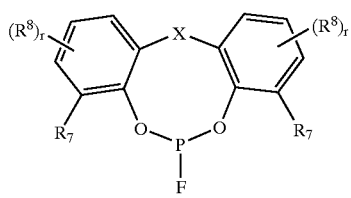

(VIII)

wherein $R^7$ represents hydrogen, chloro or $C_1$ to $C_4$ alkyl; $R^8$ represents chloro, $C_1$ to $C_4$ alkyl or $C_1$ to $C_4$ alkoxy; r is 0, 1 or 2; and X is a group having the formula

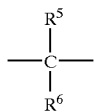

wherein $R^5$ is hydrogen, alkyl or aryl; and $R^6$ is hydrogen or alkyl; (2) rhodium, wherein the ratio of gram moles dihydrocarbyl fluorophosphite ligand to gram atoms rhodium is about 1:1 to 500:1; and (3) a Group VIII metal selected from the group consisting of platinum, cobalt, ruthenium, and palladium wherein the gram atom ratio of the Group VIII metal:rhodium metal is in the range of about 1:1 to 5:1; wherein the olefin is a mono-α-olefin of 3 to 8 carbon atoms; and the process is carried out at a temperature of 50 to 135° and the normal to iso ratio of the aldehyde product is controlled by varying the partial pressure of carbon monoxide in the reactor gas between 0.4 and 13 barg.

10. The process according to claim 9 wherein the concentration of rhodium in the solution is in the range of about 30 to 300 mg per liter; the fluorophosphite ligand has the formula

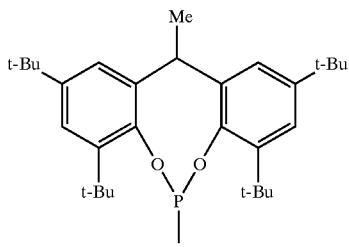

wherein t-Bu is tertiary butyl and Me is methyl; the ratio of gram moles fluorophosphite ligand to gram atoms rhodium is about 5:1 to 150:1; the olefin is a mono-α-olefin of 2 to 10 carbons atoms; and the process is carried out at a temperature of about 50 to 135° C. at a pressure in the range of 0.7 to 69 bars gauge.

* * * * *

UNITED STATES PATENT AND TRADEMARK OFFICE
CERTIFICATE OF CORRECTION

PATENT NO. : 6,906,225 B2
DATED : June 14, 2005
INVENTOR(S) : Puckette et al.

Page 1 of 1

It is certified that error appears in the above-identified patent and that said Letters Patent is hereby corrected as shown below:

Column 16,
Line 66, reads "to 69 bars gauge; $R^1$ and $R^2$ aryl groups independently" should read -- to 69 bars gauge; $R^1$ and $R^2$ are aryl groups independently --.

Column 18,
Line 19, reads, "each of $A^2$ and $A^2$ is an arylene radical having formula" should read -- each of $A^1$ and $A^2$ is an arylene radical having formula --.

Column 20,
Lines 17-28, reads " 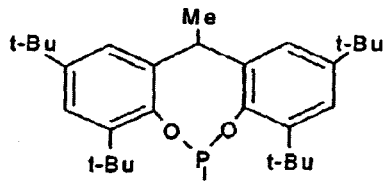 " should read

-- 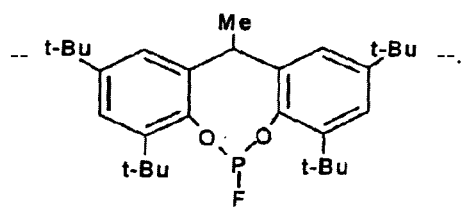 --.

Signed and Sealed this

Twenty-fifth Day of October, 2005

JON W. DUDAS
*Director of the United States Patent and Trademark Office*